United States Patent [19]

Schroder et al.

[11] Patent Number: 5,153,126
[45] Date of Patent: Oct. 6, 1992

[54] METHOD FOR CONTINUOUS PREPARATION OF HIGHLY PURE MONOGLYCERIDE

[75] Inventors: Roland Schroder, Yokohama; Kenkichi Oba, Funabashi, both of Japan

[73] Assignee: Lion Corporation, Tokyo, Japan

[21] Appl. No.: 198,578

[22] Filed: May 25, 1988

[30] Foreign Application Priority Data

May 29, 1987 [JP] Japan ................................. 62-134201

[51] Int. Cl.$^5$ .............................................. C12P 7/64
[52] U.S. Cl. ................................................... 435/134
[58] Field of Search ........................................ 435/134

[56] References Cited

U.S. PATENT DOCUMENTS 4,275,011  6/1981  Tanaka et al. ...................... 435/134

FOREIGN PATENT DOCUMENTS

| | | |
|---|---|---|
| 0191217 | 8/1986 | European Pat. Off. . |
| 0195311 | 9/1986 | European Pat. Off. . |
| 2617501 | 1/1989 | France . |
| 5049489 | 9/1973 | Japan . |
| 120285 | 10/1984 | Japan ................................. 435/134 |
| 210893 | 11/1984 | Japan ................................. 435/134 |
| 278988 | 12/1987 | Japan ................................. 435/134 |

OTHER PUBLICATIONS

*Glyceride Synthesis by Four Kinds of Microbial Lipase,* Yoshio Tsujisaka, Susumu Okumura and Mieko Iwai, Biochimica et Biophysica Acta, 489 (1977) 415-422.

*Some Characteristics of Continuous Glyceride Synthesis by Lipase in a Microporous Hydrophobic Membrane Bioreactor,* Mohammad Mozammel Hoq, Haruko Tagami, Tsuneo Yamane and Shoichi Shimizu, Agric. Biol. Chem., 49(2), 335-342, 1985.

*Enzymatic Fat Hydrolysis and Synthesis,* Warner M. Linfield, Robert A. Barauskas, Lorraine Sivieri, Samuel Serota and Robert W. Stevenson, Sr., JAOCS, vol. 61, No. 2 (Feb. 1984).

Primary Examiner—Carolyn Elmore
Attorney, Agent, or Firm—Burns, Doane, Swecker & Mathis

[57] ABSTRACT

A method for continuous preparation of highly pure monoglyceride comprises the steps of esterifying fatty acid dissolved in a nonpolar solvent at the interface between the nonpolar solvent phase and a polar solvent phase containing glycerol, water and dispersed lipase, the polar phase being located below the nonpolar phase, continuously taking out the nonpolar solvent phase, cooling the taken out phase to isolate the resulting monoglyceride by precipitation, and bringing back the remaining solution to the esterification system.

By this method, monoglycerides having high purity can be produced continuously and at low cost, and further monoglycerides of straight-chained fatty acids can preferentially obtained even though the fatty acids used contain branched fatty acids.

14 Claims, No Drawings

METHOD FOR CONTINUOUS PREPARATION OF HIGHLY PURE MONOGLYCERIDE

BACKGROUND OF THE INVENTION (1) Field of the Invention

This invention relates to a method for continuous synthesis of highly pure monoglyceride utilizing an enzymatic reaction.

(2) Prior Art

Heretofore monoglycerides have mainly been synthesized by either a batch method or a continuous method. Batch methods in which glycerin and a fatty acid are stirred with heating in the presence of a chemical catalyst or an enzyme have the advantage of high reaction rate but have the disadvantage that the catalyst (or enzyme) is hard to isolate after the reaction. On the other hand, according to continuous methods, a reaction mixture consisting of glycerol and a fatty acid is stirred in or passed through a reactor containing an enzyme immobilized on a thin film or a solid carrier to carry out the esterification reaction. These continuous methods have the advantage that the enzyme can be repeatedly and safely used for a long time, but have disadvantages in that (i) the contact area for the reaction is inadequate, (ii) reaction rate is lowered because of loss or lowering of activity at immobilization and (iii) the cost of immobilizing agents is high and the like. Further, when a chemical catalyst is used, esterification proceeds regardless of whether the used fatty acid is of straight-chained or branched structure, and in a case where there is no need for branched fatty acid monoglycerides, the cost for purification of monoglycerides is high.

Furthermore, even when an enzyme which preferentially synthesizes monoglycerides is used in batch methods or continuous methods, it is impossible at present to synthesize monoglycerides alone. Thus, no method for continuously and effectively obtaining highly pure monoglycerides has been known.

SUMMARY OF THE INVENTION

The object of the invention is to provide a method for continuous preparation of monoglycerides by which monoglycerides can be inexpensively synthesized at a reaction rate comparable to a batch method using an enzyme and moreover, highly pure monoglycerides can be readily and inexpensively isolated from the reaction mixture.

The present invention has been achieved based on the finding that the above problems can effectively be solved by a method in which there is used a two layer system consisting of a lower layer containing glycerol and lipase and an upper layer containing a fatty acid, an esterification reaction is carried out at the interface of the two layers utilizing an enzymatic action of lipase, the upper layer is taken out continuously and cooled to precipitate the formed monoglycerides, and the remaining solution containing the unreacted fatty acid and a small amount of di- and triglycerides is continuously brought back to the reaction system.

That is, the present invention provides a method for continuous preparation of highly pure monoglyceride, which comprises the steps of esterifying fatty acid dissolved in a nonpolar solvent at the interface between the nonpolar solvent phase and a polar solvent phase containing glycerol, water and dispersed lipase, the polar phase being located below the nonpolar phase, continuously taking out the nonpolar solvent phase, cooling the taken out phase to isolate the resulting monoglyceride by precipitation, and bringing back the remaining solution to the esterification system.

PREFERRED EMBODIMENTS OF THE INVENTION

Various fatty acids can be used in the invention, but there can be suitably used saturated or unsaturated fatty acids having 5 to 25 carbon atoms, preferably 10 to 20 carbon atoms. Examples of the fatty acids include decanoic acid, undecanoic acid, dodecanoic acid, tridecanoic acid, tetradecanoic acid, pentadecanoic acid, hexadecanoic acid, heptadecanoic acid, octadecanoic acid, oleic acid, nonadecanoic acid, eicosanoic acid, etc. (including various branched fatty acids). These compounds can be used alone or as a mixture of 2 or more of them.

As the nonpolar solvents used for dissolving the above fatty acids in the invention, there can be mentioned hydrocarbons having 5 or more, preferably 6 to 10 carbon number which, in the esterification reaction, dissolve the above fatty acids and glycerides as the product, but do not dissolve lipase, glycerol and various salts as a stabilizer of lipase and do not inactivate the lipase to be used, for example n-hexane, n-heptane, n-octane, n-decane, cyclohexane, methylcyclohexane, etc.

Though fatty acid used in the reaction can be dissolved in the above nonpolar solvent in an arbitrary amount, the concentration of fatty acid is suitably in the range of 1 to 60 mg/ml, preferably 1 to 30 mg/ml, and, for example, when pentadecanoic acid is esterified, the concentration thereof is preferably maintained at 18 mg/ml or less (in the case of using cyclohexane) or 7 mg/ml or less (n-heptane), taking the precipitation step of the monoglyceride into account.

In the present invention, the reaction system is composed of the above nonpolar solvent phase as the upper layer and a water-containing glycerin phase containing lipase as the lower layer, and an esterification reaction is carried out at the interface of the two layers.

As lipase to be used, there can be mentioned hydrolases derived from thermophilic or mesophilic microorganisms, for example lipases derived from *Mucor miehi, Rhizopus delemar, Penicillium cyclopium* and *Pseudomonas fluorescens*. Lipase sp 225 (derived from Mucor miehi, 210 unit/mg) manufactured by Novo Industri Co.; and Lipase D-10 (derived from *Rhizopus delemar*, 275 unit/mg), Lipase G (derived from *Penicillium cyclopium*, 60 unit/mg) and Lipase P (derived from the genus Pseudomonas 2000 unit/mg) manufactured by Amano Pharmaceutical Co., Ltd., for example, are commercially available. The concentration of these lipases in water-containing glycerol is arbitrary, but, for example, the concentration is suitably 1 to 50 mg/ml, preferably 2 to 15 mg/ml in the water-containing glycerol. As the water-containing glycerol used in the invention, there can be mentioned those containing 2 to 20% v/v, preferably 4 to 10% v/v water.

The esterification reaction in the invention is suitably carried out at a reaction temperature of 20° to 75° C., for example at 20° to 40° C. in the case of using lipase derived from *Rhizopus delemar* and at 20° to 70° C. in the case of using lipase derived from *Pseudomonas fluorescens*. Therefore, though particular methods for heating are unnecessary when the reaction is carried out at room temperature, it is suitable to maintain the esterification temperature constant using a heating apparatus in order to prevent lowering of temperature owing to circulation of the cooled nonpolar solvent to the esterification system. In this regards, the flow rate is preferably 1 to 120 ml/h. Further, since the water amount in the reaction system becomes larger with the progress of the esterification reaction, it is desirable to suitably maintain the reation rate by controlling the water content in the glycerol to 2 to 20% v/v using a molecular sieve (for example, 0.3 nm). Further, it is desirable to accelerate the esterification reaction at the interface of the nonpolar solvent phase and the water-containing glycerol phase by stirring using a known stirring method. In this connection, it is desirable to stir with care taken not to disturb the interface too much.

Various salts, complexing agents, particles (inorganic or organic) or the like having a lipase-stabilizing action can be dissolved or dispersed in the water-containing glycerol phase in the present invention.

Since mono-, di- and triglycerides formed by the above esterification reaction are dissolved in the nonpolar solvent phase in the invention, the nonpolar solvent phase is taken out from the reaction system by a known method and cooled to precipitate the monoglyceride. That is, the monoglyceride is separated out of the nonpolar solvent phase. The precipitation temperature varies depending on the fatty acid and nonpolar solvent to be used, the melting point of the product and the desired purity of the product, and is appropriately set. In this connection, it is desirable to cool down the reaction system to the temperature between 4° and 25° C.

Next, the nonpolar solvent after precipitation and removal of monoglyceride is recycled to the reaction system.

At this step, it is preferable that the nonpolar phase be circulated continuously via a vial maintained at a temperature lower than the reaction vessel so as to isolate the monoglyceride by precipitation.

According to the above method, fatty acid monoglyceride of a high purity, for example a purity of 75% or more, preferably 90% or more can be readily prepared.

Since the enzyme exists in polar glycerol, and does not dissolve in a nonpolar solvent, loss of enzyme by the reaction is extremely low in the present invention. Further, since specificity of monoglyceride formation does not depend on site specificity of the lipase but on the precipitation step for monoglyceride, low-priced nonspecific enzymes can be used without purification. Further, since the nonpolar solvent and fatty acid circulate in a closed reaction circuit, there is substantially no loss of the fatty acid, which is different from a batch method.

As can be seen from the foregoing, monoglycerides of high purity can be produced continuously and at low cost by the invention. Further, since heat generated from the cooling apparatus can be used for heating of the enzyme reactor, energy costs in the present method are low, and thus the present method is suitable as a method for continuous industrial production of highly pure monoglycerides.

Monoglycerides synthesized in the invention are highly pure, and can widely be used as emulsifiers, food additives, hair-restoring components (such as pentadecane monoester), etc.

The present invention is further described with reference to examples.

EXAMPLE 1

A phase consisting of a solution of 330 mg of n-pentadecanoic acid in 55 ml of n-octane (concentration 6 mg/ml) was formed on a lower layer consisting of a dispersion of 105 mg of lipase (Lipase G manufactured by Amano Pharmaceutical Co., Ltd.) in 7.5 ml of glycerol containing 4% v/v water and 10 mM $CaCl_2$. Esterification reaction was carried out at the interface of the two phases with stirring at 50° C. using a magnetic stirrer with care taken not to disturb the interface. The nonpolar solvent phase was circulated at a flow rate of 117 ml/h between the reactor and a crystallizing bottle which was maintained at 4° C., and the precipitated pentadecanoic acid monoglyceride was isolated by ordinary filtration. The water content of the glycerol phase was controlled with a 0.3 nm molecular sieve, and as a result, the lipase kept 60% of the initial activity after the reaction at 50° C. for 40 hours. In the meantime, pentadecanoic acid was further added every 8 hours to maintain its concentration at 6 mg/ml, whereby 1177 mg of pentadecanoic acid monoglyceride having a purity of 95% was obtained.

EXAMPLE 2

Lipase (Lipase G) (150 mg) was dispersed in 15 ml of glycerol containing 4% v/v water and 10 mM $CaCl_2$ to form a lower layer, a solution of 240 mg of stearic acid in 80 ml of n-octane (concentration 3 mg/ml) was provided thereon as the upper layer, and the two layers were stirred at 50° C. using a magnetic stirrer to carry out an esterification reaction at the interface between the two layers. The nonpolar solvent phase was circulated at a flow rate of 117 ml/h between the reactor and a crystallizing bottle which was maintained at 20° C., and the precipitated stearic acid monoglyceride was isolated by an ordinary filtration method. As the result of thin layer chromatography and liquid chromatography, it was shown that stearic acid monoglyceride of 96% purity can be synthesized at a rate of 0.5 g/g Lipase G·hour.

EXAMPLE 3

Lipase (Lipase D10 manufactured by Amano Pharmaceutical Co., Ltd.) (60 mg) was dispersed in 15 ml of glycerol containing 8% v/v of 20 mM citrate buffer (pH 5.5) and 100 mM $CaCl_2$ to form a lower layer, a solution of 375 mg of n-pentadecanoic acid in 50 ml of n-hexane (concentration 7.5 mg/ml) was provided thereon as the upper layer, and the two layers were stirred at 40° C. to carry out an esterification reaction at the interface between the two layers. The crystallizing bottle was maintained at 4° C. to obtain pentadecanoic acid monoglyceride. As a result, it was confirmed that pentadecanoic acid of 95% purity was synthesized.

EXAMPLE 4

Lipase (Lipase G) (150 mg) was dispersed in 15 ml of containing 4% v/v water and 10 mM $CaCl_2$ to form a lower layer, a solution of 480 mg of lauric acid in 80 ml of n-octane (concentration 6 mg/ml) was provided thereon as the upper layer, and the two layers were stirred at 50° C. using a magnetic stirrer to carry out an esterification reaction at the interface between the two layers. The nonpolar solvent phase was circulated at a flow rate of 117 ml/h between the reactor and a crystallizing bottle which was maintained at 0° C., and the precipitated lauric acid monoglyceride was isolated by an ordinary filtration method.

EXAMPLE 5

Lipase (Lipase D10) (30 mg) was dispersed in 15 ml of glycerol containing 4% v/v water and 10 mM CaCl$_2$ to form a lower layer, a solution of 125 mg of n-pentadecanoic acid in 25 ml of n-octane (concentration 5 mg/ml) was provided thereon as the upper layer, and the two layers were stirred at 40° C. using a magnetic stirrer to carry out an esterification reaction at the interface between the two layers. The nonpolar solvent phase was circulated at a flow rate of 117 ml/h between the reactor and a crystallizing bottle which was maintained at 4° C., and the precipitated pentadecanoic acid monoglyceride was isolated by an ordinary filtration method.

EXAMPLE 6

A phase consisting of a solution of 320 mg of n-pentadecanoic acid in 40 ml of methylcyclohexane (concentration 8 mg/ml) was formed on a lower layer consisting of a dispersion of 12 mg of lipase (Lipase p manufactured by Amano Pharmaceutical Co., Ltd.) in 6 ml of glycerol containing 8% v/v water and 1 mM CaCl$_2$. Esterification reaction was carried out at the interface of the two phases with stirring at 70° C. using a magnetic stirrer (with care taken not to disturb the interface.) The nonpolar solvent phase was circulated at a flow rate of 20 ml/h between the reactor and a crystallizing bottle which was maintained at 18° C., and the precipitated pentadecanoic acid monoglyceride was isolated by ordinary filtration.

In the meantime, pentadecanoic acid was further added to maintain its concentration at 8 mg/ml, whereby 480 mg of pentadecanoic acid monoglyceride having a purity of 95% was obtained after 6.5 hours.

EXAMPLE 7

Lipase (Lipase P manufactured by Amano Pharmaceutical Co., Ltd.) (75 mg) was dispersed in 6 ml of glycerol containing 10% v/v water and 1 mM CaCl$_2$ to form a lower layer, a solution of 480 mg of pentadecanoic acid (consisting of 68% of n-pentadecanoic acid and 32% of isopentadecanoic acid) in 40 ml of methylcyclohexane (concentration 12 mg/ml) was provided thereon as the upper layer, and the two layers were stirred with a magnetic stirrer taking care not to disturb the interface of the two layers, thus carrying out an esterification reaction. The nonpolar solvent layer was circulated at a flow rate of 60 ml/h between the reactor and a crystallizing bottle which was maintained at 20° C. to precipitate pentadecanoic acid monoglyceride, while the concentration of pentadecanoic acid was maintained at 12 mg/ml. Seven hours thereafter, 316.8 mg of pentadecanoic acid monoglyceride of 93% purity was obtained. The content of isopentadecanoic acid in the pentadecanoic acid which was recycled in the reaction system was increased finally up to 41%. It was found by gas chromatography of the methyl-esterified derivatives of the product that only 0.5% of isopentadecanoic acid was contained in the product. This reveals that lipase does not selectively catalyze esterification of branched isopentadecanoic acid.

EXAMPLE 8

Lipase (Lipase G manufactured by Amano Pharmaceutical Co., Ltd.) (75 mg) was dispersed in 6 ml of glycerol containing 10% v/v water and 1 mM CaCl$_2$ to form a lower layer, a solution of 480 mg of pentadecanoic acid (consisting of 68% of n-pentadecanoic acid and 32% of isopentadecanoic acid) in 40 ml of n-hexane (concentration 12 mg/ml) was provided thereon as the upper layer, and the two layer were stirred at 50° C. using a magnetic stirrer with care taken not to disturb the interface of the two layers, thus carrying out an esterification reaction at the interface. The nonpolar solvent phase was circulated at a flow rate of 60 ml/h between the reactor and a crystallizing bottle which was maintained at 20° C. to precipitate pentadecanoic acid monoglyceride, while the concentration of pentadecanoic acid was maintained at 12 mg/ml. Seven hours thereafter 250 mg of pentadecanoic acid monoglyceride of 95% purity was obtained. Gas chromatographic analysis of a methyl-esterfied derivative of the product revealed that only 0.4% of isopentadecanoic acid was contained in the product.

COMPARATIVE EXAMPLE

Pentadecanoic acid (consisting of 70% of n-pentadecanoic acid and 30% of isopentadecanoic acid) (12.1 g) and 13.8 g of glycerol were placed in a 50 ml flask, and further 0.2% of zinc oxide was added as a catalyst, followed by stirring with a stirring rod at 200° C. for 5 hours. Components of the product as determined by gas chromatography were 56% of monoglyceride, 32.0% of diglyceride, 1.0% of triglyceride, 10.7% of glycerol and 0.5% of pentadecanoic acid. The product was subjected to molecular distillation 5 times and again subjected to gas chromatographic analysis. As a result the components were 96.4% of monoglyceride, 1.7% of diglyceride, 1.5% of glycerol and 0.4% of pentacanoic acid. The product was methyl-esterified and composition of n-pentadecanoic acid and isopentadecanoic acid was determined by gas chromatography to be 70.5:29.5.

What is claimed is:

1. A method for continuous preparation of highly pure monoglyceride, which comprises the steps of esterifying fatty acid dissolved in a nonpolar solvent at the interface between the nonpolar solvent phase and a polar solvent phase containing glycerol, water and dispersed lipase, the polar phase being located below the nonpolar phase, continuously taking out the nonpolar solvent phase comprising a mixture of unreacted fatty acid, resulting monoglyceride, diglyceride and triglyceride, cooling the taken out phase to isolate the resulting monoglyceride by precipitation, and bringing back the remaining solution to the esterification system.

2. The method of claim 1 wherein a concentration of lipase in the water-containing glycerol phase is 1 to 50 mg/ml.

3. The method of claim 1 wherein water content in the water-containing glycerol phase is 2 to 20% v/v.

4. The method of claim 1 wherein the fatty acid is saturated or unsaturated fatty acid having 5 to 25 carbon number.

5. The method of claim 1 wherein the nonpolar solvent is a hydrocarbon having a carbon number of 5 or more which, in the esterification reaction, dissolves the fatty acid and glyceride as the product, but does not dissolve lipase, glycerol and any stabilizer of lipase used and does not inactivate lipase.

6. The method of claim 1 wherein a concentration of the fatty acid in the nonpolar solvent phase is 1 to 60 mg/ml.

7. The method of claim 1 wherein the esterification reaction is carried out at 20° to 75° C.

8. The method of claim 1 wherein the nonpolar solvent phase is circulated between the reactor and a crystallizing bottle.

9. The method of claim 8 wherein the recycle flow rate is 1 to 120 ml/h.

10. The method of claim 1 wherein the cooling temperature is 4° to 25° C.

11. The method of claim 1 wherein water content of the water-containing glycerol phase is controlled with a molecular sieve at 2 to 20% v/v during the reaction.

12. The method of claim 1 wherein the water-containing glycerol phase further contains a stabilizer of lipase.

13. The method of claim 1 wherein the fatty acid contain branched fatty acid and straight-chained fatty acid, and the straight-chained fatty acid is preferentially esterified with glycerol.

14. The method of claim 1 wherein the esterification reaction is carried out at the interface with stirring in such manner that the interface is not disturbed too much.

* * * * *